United States Patent [19]

Sloma et al.

[11] Patent Number: 5,294,542
[45] Date of Patent: Mar. 15, 1994

[54] RESIDUAL PROTEASE-III

[75] Inventors: Alan Sloma, Watertown; Gerald A. Rufo, Jr., Burlington; Janice Pero, Lexington, all of Mass.

[73] Assignee: Omnigene, Inc., Cambridge, Mass.

[21] Appl. No.: 671,376

[22] Filed: Mar. 19, 1991

[51] Int. Cl.[5] ............................................. C12P 21/06
[52] U.S. Cl. .................................... 435/69.1; 435/222; 435/252.31; 435/252.5; 435/839; 435/320.1; 536/23.2; 935/38; 935/44
[58] Field of Search .................... 435/69.1, 68.1, 172.3, 435/221, 252.31, 252.3; 536/23.2

[56] References Cited

U.S. PATENT DOCUMENTS

| | | | |
|---|---|---|---|
| 4,828,994 | 5/1990 | Fahnestock et al. | 435/172.3 |
| 4,946,789 | 8/1990 | Udaka et al. | 435/252.3 |

FOREIGN PATENT DOCUMENTS

| | | | |
|---|---|---|---|
| 0257189 | 3/1988 | European Pat. Off. | 435/252.3 |
| 0396817 | 5/1990 | European Pat. Off. | 435/252.31 |
| 8601825 | 3/1987 | PCT Int'l Appl. | 435/172.3 |
| WO89/10976 | 11/1989 | World Int. Prop. O. | |

OTHER PUBLICATIONS

Kawamura et al., "Construction of a *Bacillus subtilis* Double Mutant Deficient in Extracellular Alkaline and Neutral Proteases," J. of Bacteriology 160(1):442–444 (1984).

Koide et al., "Cloning and Sequencing of the Major Intracellular Serine Protease Gene of *Bacillus subtilis*," J. of Bacteriology 167(1):110–116 (1986).

Stahl et al., "Replacement of the *Bacillus subtilis* Subtilisin Structural Gene with an In Vitro-Derived Deletion Mutation," J. of Bacteriology 158(2):411–418 (1984).

Yang et al., "Cloning of the Neutral Protease Gene of *Bacillus subtilis* and the Use of the Cloned Gene to Create an In Vitro-Derived Deletion Mutation," J. of Bacteriology 160(1):15–21 (1984).

*Primary Examiner*—Robert A. Wax
*Assistant Examiner*—D. Schmickel
*Attorney, Agent, or Firm*—Fish & Richardson

[57] ABSTRACT

A Bacillus cell containing a mutation in the residual protease III (rp-III) gene resulting in the inhibition of the production by the cell of proteolytically active RP-III.

19 Claims, 6 Drawing Sheets

```
RP-III      I G A N D A W D L G Y T G K G I K V A I I D T G V E
COMPOSITE I - A - - A W - L G Y T G K G I K V A - I D T G V E
                                                    ^
                                            ACTIVE CENTER ASP

COMPOSITE HOMOLOGY  - 81%
              BPR HOMOLOGY        - 65%
```

FIG. 1

|  | 1 | 2 | 3 | 4 | 5 | 6 | 7 | 8 |
|---|---|---|---|---|---|---|---|---|
| H₃N | -MET- | ASP- | ASP- | SER- | ALA- | PRO- | TYR- | ILE- |
| 5' | -ATG | GAT- | GAT- | TCT- | GCA- | CCG- | TAT- | ATT- |

|  | 9 | 10 | 11 | 12 | 13 | 14 | 15 | 16 |
|---|---|---|---|---|---|---|---|---|
|  | GLY- | ALA- | ASN- | ASP- | ALA- | TRP- | ASP- | LEU- |
|  | GGA- | GCA- | AAT- | GAT- | GCA- | TGG- | GAT- | CTT- |

|  | 17 | 18 | 19 | 20 | 21 | 22 | 23 | 24 |
|---|---|---|---|---|---|---|---|---|
|  | GLY- | TYR- | THR- | GLY- | LYS- | GLY- | ILE- | LYS- |
|  | GGA- | TAT- | ACA- | GGA- | AAA- | GGA- | ATT- | AAA- |

|  | 25 | 26 | 27 | 28 | 29 | 30 | 31 | 32 |
|---|---|---|---|---|---|---|---|---|
|  | VAL- | ALA- | ILE- | ILE- | ASP- | THR- | GLY- | VAL- |
|  | GTT- |  |  |  |  |  |  |  |

|  | 33 | 34 | 35 |
|---|---|---|---|
|  | GLU- | TYR- | ASN- |

```
001 ATC TTT CAC ATT TTT TCT AAA TAC AAA GGG GGA AAC ACA TTG AAA AAG GGG ATC ATT CGC
    ile phe his ile phe ser lys tyr lys gly gly asn thr met lys lys gly ile ile arg 061 TTT CTG CTT GTA AGT TTC GTC TTA TCT AAA GGG GGA AAC ACA TTG AAA AAG GGG ATC ATT CGC
    phe leu leu val ser phe val leu ser ala phe                 ile  thr gly  val gln (Note: row 061 actual)
061 TTT CTG CTT GTA AGT TTC GTC TTA TCT GCG TTA TCC ACA ATT GGC ACG GGC GTT CAG
    phe leu leu val ser phe val leu ser ala leu ser thr ile gly thr gly val gln 121 GCA GCT CCG TCT TCA AGC GCT ACG AAA AAA TCG GAT CTG GAA GAG GTA GCC TTC GGT GAT
    ala ala pro ser ser ala thr lys lys ser asp leu glu glu val ala phe gly asp 181 ATC GAT ATG ACG ACA AGC AAA ACA ACC GTT ATA GTG GAA GAA TTA AAA GAA AAA TCC TTG
    ile asp met thr thr ser lys thr thr val ile val glu glu leu lys glu lys ser leu 241 GCA GAA GCG AAG GAA GGA CAA AGC ATG TCG AAA AGC ATG CTG AAA ACC GCT CGC ACC
    ala glu ala lys glu gly gln ser met ser lys ser met leu lys thr ala arg thr 301 AAA GCA AAA AAC AAC GCA GTG AAA CTT AAA GGA AAC GTA ATG AAA CGG GAA TAT GAG
    lys ala lys asn asn ala val lys leu lys gly asn val met lys arg glu tyr glu 361 CAG GTA TTC TCA GGC TTC TCT ATG AAG CTT CCA AAT GAG GCT AAT ACA AAA CTT CTA GCG
    gln val phe ser gly phe ser met lys leu pro asn glu ala asn thr lys leu leu ala 421 GTA GAC GTT AAG GCA GTG TAC GTG GTA TAC CCG AAC GTC ACA TAT TAT AAA ATG AAG GAT
    val asp val lys ala val tyr val val tyr pro asn val thr tyr tyr lys met lys asp 481 AAA GAC GTC ACA ATC TCC GAA GAC GCC GTA TCT CCG CAA ATG GAT GAC AGT GCG CCT TAT
    lys asp val thr ile ser glu asp ala val ser pro gln met asp asp ser ala pro tyr 541 ATC GGA GCA AAC GAT GCA TGG GAT TTA GGC TAC TTA ACA GGA AAA AAG ATC GTG GCG ATT
    ile gly ala asn asp ala trp asp leu gly tyr leu thr gly lys lys ile val ala ile 601 ATT GAC ACT GGG GTT GAA TAC CAC CCA GAT CTG AAG AAA AAC TTT GGA CAA TAT AAA
    ile asp thr gly val glu tyr his pro asp leu lys lys asn phe gly gln tyr lys 661 GGA TAC GAT TTT GTG GAC AAT GAT TAC CCA GAT TAC CCA AAA GAA ACC GGC GAT CCG AGG
    gly tyr asp phe val asp asn asp tyr pro asp tyr pro lys glu thr gly asp pro arg 721 GGC GAG GCA ACT GAC CAT GGT ACA CAC GTA GCC GGA ACT GTG GCA AAC GGA ACG ATT
    gly glu ala thr asp his gly thr his val ala gly thr val ala asn gly thr ile 781 AAA GGC GTA GCG CCT GAT GCC ACA CTT CTT GCT TAT CGT GTG TTA GGG CCT GGC GGA AGC
    lys gly val ala pro asp ala thr leu leu ala tyr arg val leu gly pro gly gly ser
```

FIG. 4B

```
 841 GGC ACA GAA AAC GTC ATC GCG GGC GTG GAA CGT GCA GTG CAG GAC GGG GCA GAT GTG
     gly thr glu asn val ile ala gly val glu arg ala val gln asp gly ala asp val 901 ATG AAC CTG TCT CTC GGA AAC TCT TTA AAC CCG GAC TGG ACA AGC ACA GCG CCG CTT
     met asn leu ser leu gly asn ser leu asn pro asp trp thr ser thr ala pro leu 961 GAC TGG GCC ATG TCA GAA GGA GTT GCT GTT ACC TCA AAC GGC AAC AGC GGA CCG AAC
     asp trp ala met ser glu gly val ala val thr ser asn gly asn ser gly pro asn 1021 GGC TGG ACA GTC GGA TCG CCG GGC ACA AGA GAA GCG TCT GTC GGT GCG ACT CAG
     gly trp thr val gly ser pro gly thr arg glu ala ser val gly ala thr gln 1081 CTG CCG CTC AAT GAA TAC GCC GTC ACT TTC GGC TCC TAC TCA GCA GTG ATG GGC
     leu pro leu asn glu tyr ala val thr phe gly ser tyr ser ala val met gly 1141 TAC AAC AAA AAA GAG GAC GTC AAA GCG CTC GAA AAT GAT AAC AAA CTG GAG GTT GAA GTT GTC
     tyr asn lys lys glu asp val lys ala leu asn asp asn lys leu glu val val val 1201 GGA ATC GGC GAA GCA AAG TTT GAA GGG GTT ACA GAC GGC AAA AAA GCC GGT GCA ATC
     gly ile gly glu ala lys phe glu gly val thr asp gly lys lys ala gly ala ile 1261 AAA CGA GGC AGC GTG TAT GCA ATT GCA TTT GTG GAT AAA CTC TCT AAT GAA GCC ATG TCT
     lys arg gly ser val tyr ala ile ala phe val asp lys leu ser asn glu ala met ser 1321 GGC ATG GTT GTG AAG ATT AAC CTT TTA GAA GAC GGC ACG AGC GCC CTG AAA GCT
     gly met val val lys ile asn leu leu glu asp gly thr ser ala leu lys ala 1381 GTC CCA ACG ACA ACA TTC AAG TTG ACG GTC ACG TCA AAA GCG CTC GAA CAA GTC GCT
     val pro thr thr thr phe lys leu thr val thr ser lys ala leu glu gln val ala 1441 GGT GAG ACA ACA CGC GGC CCT GTT ATG GAT ACG TGG ATT AAG CCT GAC ATT TCC GCG
     gly glu thr thr arg gly pro val met asp thr trp ile lys pro asp ile ser ala 1501 GAT TTC TCA TCA CGC GGC CCT GTT ATG GAT ACG TGG ATT AAG CCT GAC ATT TCC GCG
     asp phe ser ser arg gly pro val met asp thr trp ile lys pro asp ile ser ala 1561 CCA GGG GTC AAT ATC GTG AGC ACG ATC GCA CAC GAT CCT CAT TAC GGC TAC
     pro gly val asn ile val ser thr ile ala his asp pro his tyr gly tyr 1621 GGA TCA AAA CAA GGA ACA AGC ATG GCA TCG GCC GGA GCG GTT GCC ATT
     gly ser lys gln gly thr ser met ala ser ala gly ala val ala ile
```

```
1681  AAA CAA GCC AAA CCA AAG TGG AGC GTT GAA CAG ATT AAA GCC GCC ATC ATG AAT ACC GCT
      lys gln ala lys pro lys trp ser val glu gln ile lys ala ala ile met asn thr ala 1741  GTC ACT TTA AAG GAT AGC GAT AGC GAA GTA GAG TAT CCG CAT AAC GCT CAA GGC GCA GGC AGC
      val thr leu lys asp ser asp ser glu val glu tyr pro his asn ala gln gly ala gly ser 1801  GCA AGA ATT ATG AAC GCA ATC AAA GCC GAT TCG CTC GTC TCA CCT GGA AGC TAT TCA TAC
      ala arg ile met asn ala ile lys ala asp ser leu val ser pro gly ser tyr ser tyr 1861  GGC ACG TTC TTG AAG GAA AAC GGA AAT AAA AAT GAA ACA ACG TTT ACG ATT GAA AAT
      gly thr phe leu lys glu asn gly asn lys asn glu thr thr phe thr ile glu asn 1921  CAA TCT TCC ATT AGA AAG TCA TAC CTT GAA CTT TAT TCA TTT AAT GGC AGC ATT GCA TCC
      gln ser ser ile arg lys ser tyr leu glu leu tyr ser phe asn gly ser ile ala ser 1981  ACA TCC GGC ACA AGC CGT GTT ATT CCG GCA CAT CAA ACC GGG AAA GCC ACT GCA AAA
      thr ser gly thr ser arg val ile pro ala his gln thr gly lys ala thr ala lys 2041  GTA AAG GTC AAT ACG AAG ACA GCT GGC ACC TTG ATT GAA GGA ACG GTT ATC GTC AGA
      val lys val asn thr lys thr ala gly thr leu ile glu gly thr val ile val arg 2101  GAA GGA AAA ACG GTC TCT GTC AAG GTA AGC GAA TCT GTA CAA GGT ACC TAT CAA GAG CCC GAT TAT
      glu gly lys thr val ser val lys val ser glu ser val gln gly thr tyr gln glu pro asp tyr 2161  CCG AGA GTC ACA TCT CCT GCG GCG GAA GAG CTG GCG TTC ACC TAT AAA GGT TAC CAG TAC TTT GAC ATT GAA
      pro arg val thr ser pro ala ala glu glu leu ala phe thr tyr lys gly tyr gln tyr phe asp ile glu 2221  ACC TAC CTT CCT CCT GCG GCC ATT TAT AAA CAA GAT CAA AAC CTT GAC
      thr tyr leu pro pro ala ala ile tyr lys gln asp gln asn leu asp 2281  TTC GCA GGC CAA GGC GGC GGA GCG CCG CCG GGA GAG TAC CAG TAT TAC TTG CTC GCA TAT
      phe ala gly gln gly gly gly ala pro pro gly glu tyr gln tyr tyr leu leu ala tyr 2341  GAC GGC ACG ATT AAT GGC AAG ACC AGC CAG GTT ACC TTG ACC GAA GAA CCT TTC GTT GAA TAA
      asp gly thr ile asn gly lys thr ser gln val thr leu thr glu glu pro phe val glu OCH 2401  GCC GCG AAC GCG GAT TCG GCA GGG CTT TTT AAA GAT CAG TCA GCA AAC GCC TCC TGC AAT AAG GGA TAC G
      ala ala asn ala asp ser ala gly leu phe lys asp gln ser ala asn ala ser cys asn lys gly tyr
```

FIG. 4C

RESIDUAL PROTEASE-III

BACKGROUND OF THE INVENTION

This invention relates to Bacillus strains useful for the expression and secretion of desired polypeptides (as used herein, "polypeptide" means any useful chain of amino acids, including proteins).

Bacillus strains have been used as hosts to express heterologous polypeptides from genetically engineered vectors. The use of a Gram positive host such as Bacillus avoids some of the problems associated with expressing heterologous genes in Gram negative organisms such as E. coli. For example, Gram negative organisms produce endotoxins which may be difficult to separate from a desired product. Furthermore, Gram negative organisms such as E. coli are not easily adapted for the secretion of foreign products, and the recovery of products sequestered within the cells is time consuming, tedious, and potentially problematic. In addition, Bacillus strains are non-pathogenic and are capable of secreting proteins by well-characterized mechanisms.

A general problem in using Bacillus host strains in expression systems is that they produce large amounts of proteases which can degrade heterologous polypeptides before they can be recovered from the culture media. The production of the majority of these proteases occurs at the end of the exponential growth phase. At this time, conditions of nutrient deprivation exist and the cells are preparing for sporulation. The two major extracellular proteases are an alkaline serine protease (subtilisin), the product of the apr gene, and a neutral metalloprotease, the product of the npr gene. Secretion of these proteases occurs into the medium, whereas the major intracellular serine protease, Isp-I, is produced within the cells. Other investigators have created genetically altered Bacillus strains that produce below normal levels of one or more of these three proteases. These strains still produce high enough levels of protease to cause the degradation of heterologous gene products prior to purification.

Stahl et al. (J. Bact., 1984, 158:411) disclose a Bacillus protease mutant in which the chromosomal subtilisin structural gene was replaced with an in vitro derived deletion mutation. Strains carrying this mutation had only 10% of the wild-type extracellular production of protease activity. Yang et al. (J. Bact., 1984, 160:15) disclose a Bacillus protease mutant in which the chromosomal neutral protease gene was replaced with a gene having an in vitro derived deletion mutation. Fahnestock et al. (WO 86/01825) describe the construction of Bacillus strains lacking subtilisin activity by replacing the native chromosomal gene sequence with a partially homologous DNA sequence containing an inserted inactivating segment. Kawamura et al. (J. Bact., 1984, 160:442) disclose Bacillus strains carrying lesions in the npr and apr genes. These strains express less than 4% of the extracellular protease activity levels observed in wild-type strains. Koide et al. (J. Bact., 1986, 167:110) disclose the cloning and sequencing of the isp-1 gene and the construction of an Isp-1 negative mutant by chromosomal integration of an artificially deleted gene.

Sloma et al., 1990 J. Bact. 172:1024–1029, employed B. subtilis deleted for the three major proteases (apr, npr, isp) in order to identify three additional residual proteases (epr, bpr, mpr). Blackburn et al., WO 89/10976 also used sporulation competent apr-, npr- strains to isolate what they alledge to be a residual serine protease (rsp) which lacks amino terminal homology to known bacillus proteases.

Genetically altered strains which are deleted for both the major extracellular protease genes (apr and npr) and three residual protease genes (epr, bpr, mpr) produce virtually undetectable levels of protease activity in standard protease assays. However, a resorufin-labeled casein substrate, can be used to detect minor protease activities which are responsible for degradation of some heterologous polypeptides and proteins.

SUMMARY OF THE INVENTION

The invention provides a novel protease, RP-III, and improved Bacillus cells containing mutations in the previously uncharacterized RP-III encoding gene (vpr); the cells also preferably contain mutations in the one or more or any combination of extracellular protease encoding apr, npr. epr, bpr, and mpr genes, resulting in the inhibition by the cells of production of these proteases. The bpr and mpr genes are also known as rp-I and rp-II, respectively.

Preferably, the mutation of the invention involves a mutation in the rp-III gene (recently named vpr) which inhibits the production by the cell of the proteolytically active RP-III. (As used herein, mutation can refer to a deletion within or of the coding region of a gene, a substitution of one or more base pairs for one or more naturally occurring base pairs, or an insertion of one or more base pairs within the coding region of a gene.) Most preferably, the mutation of the invention is a deletion within the coding region of the gene, including deletion of the entire coding region; alternatively, the mutation can consist of a substitution of one or more base pairs for naturally ocurring base pairs, or an insertion within the protease coding region.

The Bacillus cells of the invention may also contain a mutation in the isp-1 gene encoding intracellular serine protease I and may, in addition, contain a mutation which blocks sporulation and thus reduces the cell's capacity to produce sporulation dependent proteases; preferably, this mutation blocks sporulation at an early stage, most preferably, this mutation is the spoOA mutation (described below). The invention further provides a method for producing stable heterologous polypeptides in a Bacillus host cell by modifying the host to contain mutations in the apr, npr, and rp-III genes and in one or more of the genes including the epr gene, the bpr gene, and the mpr (rp-II) gene. The method may include introducing into the Bacillus host cell a gene encoding a heterologous polypeptide that is modified so as to be expressed in the Bacillus host; such gene modifications may include but are not limited to a compatible promoter sequence, enhancer sequence, and/or ribosome binding site.

The invention also features purified DNA, expression vectors containing DNA, and host Bacillus cells transformed with DNA encoding RP-III; preferably, such DNA is derived from Bacillus subtilis.

The invention also features the isolation of a substantially pure previously uncharacterized residual protease (RP-III); as used herein, "substantially pure" means greater than 90% pure by weight.

The term "rp-III gene" herein means the respective gene corresponding to this designation in Bacillus subtilis, and the evolutionary homologues of this gene in other Bacillus species, which homologues, as is the case for other Bacillus proteins, can be expected to vary in minor respects from species to species. In many cases, sequence homology between evolutionary homologues is great enough so that a gene derived from one species can be used as a hybridization probe to obtain the evolutionary homologue from another species, using standard techniques. In addition, of course, those terms also include genes in which base changes have been made which, because of the redundancy of the genetic code, do not change the encoded amino acid residue or which produce conservative changes (to an amino acid of similar hydrophobicity or charge distribution) to a few amino acids.

Using the procedures described herein, we have produced Bacillus strains which are significantly reduced in their ability to produce proteases, and are therefore useful as hosts for the expression, without significant degradation, of heterologous polypeptides capable of being secreted into the culture medium. We have found that the Bacillus cells of the invention, even though containing several mutations in genes encoding related activities, are not only viable but healthy.

Any desired polypeptide can be expressed according to the invention, e.g., medically useful proteins such as hormones, vaccines, antiviral proteins, antitumor proteins, antibodies or clotting proteins; and agriculturally and industrially useful proteins such as enzymes or pesticides, and any other polypeptide that is normally degraded by RP-III.

Other features and advantages of the invention will be apparent from the following description of the preferred embodiments thereof, and from the claims.

DESCRIPTION OF PREFERRED EMBODIMENTS

The drawings will first be briefly described.

DRAWINGS

FIG. 1 is a comparison of N-terminal sequence of RP-III to a composite N-terminal sequence deduced from known B. subtilis serine protease sequences encoded by apr, epr, bpr and isp-1.

FIG. 2 is the N-terminal sequence of RP-III and corresponding sequence of the "guess-mer" oligonucleotide probe used to identify the rp-III gene.

FIG. 4 (parts A-C) is the DNA sequence of DNA encoding the rp-III gene.

GENERAL STRATEGY FOR CREATING PROTEASE DEFICIENT BACILLUS STRAINS

General Methods

Figure 3:
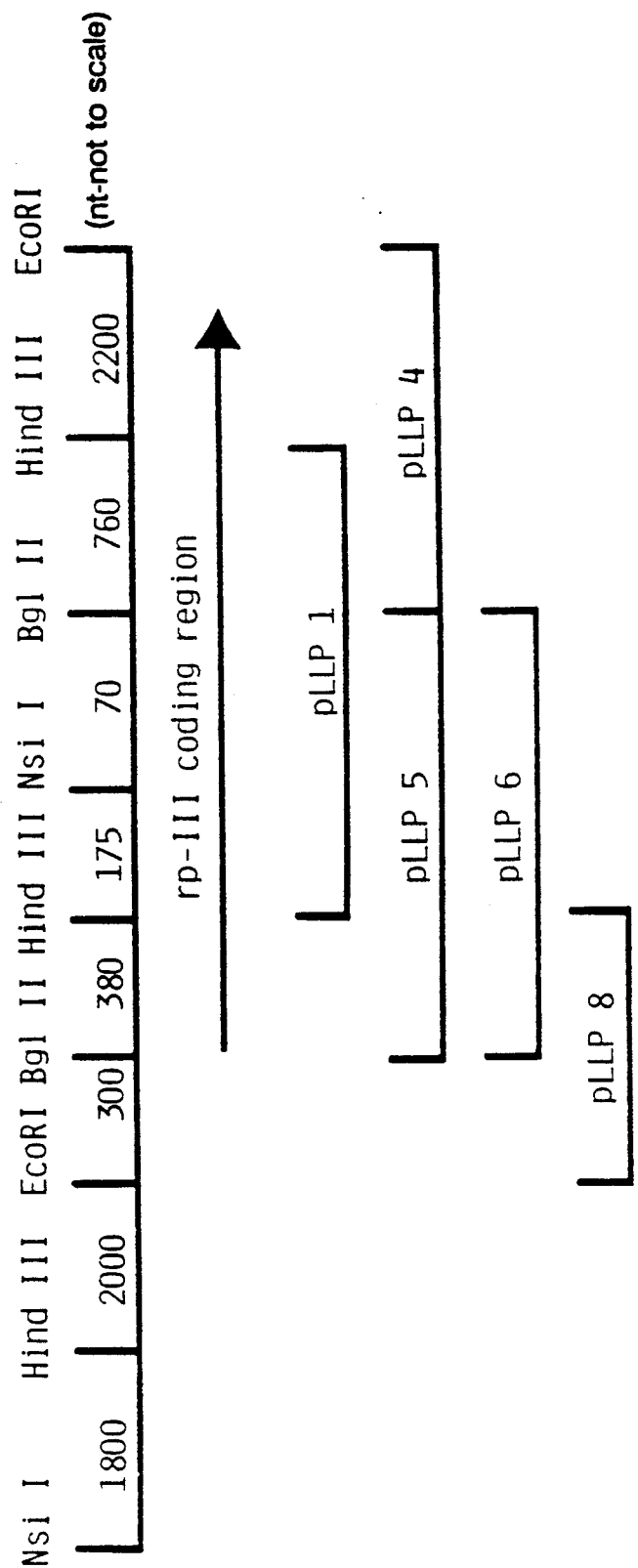
FIG. 3 is a restriction map of a DNA fragment containing the rp-III coding region and shows approximate locations of rp-III subclones.

In order to detect residual protease activity remaining in B. subtilis after removal of other known proteases, a strain must be constructed which lacks the known proteases. A Bacillus strain which is substantially devoid of extracellular proteolytic activity is described in EPA 0 369 817 A2, by Sloma et al., hereby incorporated by reference. A similar strain which contains multiple mutations which inactivate apr, npr, isp-1, epr, bpr, and mpr was prepared and assayed for residual serine protease activity using resorufin-labeled casein (Boehringer-Mannheim) as a substrate. Residual serine protease RP-III was detected in the multiply mutated strain; its activity was monitored throughout purification using the same substrate. The purification and characterization of RP-III and isolation of the gene encoding RP-III are described below, along with a procedure for generating a Bacillus strain containing a mutation which inactivates the RP-III-encoding gene.

General Methods

Construction of a multiply-mutated Bacillus strain is described by Sloma et al EPA 0 369 817 A2. Isolation of B. subtilis chromosomal DNA was as described by Dubnau et al., (1971, J. Mol. Biol., 56: 209). B. subtilis strains were grown on tryptose blood agar base (TBAB) (Difco Laboratories) or minimal glucose medium and were made competent by the procedure of Anagnostopoulos et al., (J. Bact., 1961, 81: 741). E. coli JM107 was grown and made competent by the procedure of Hanahan (J. Mol). Biol., 1983, 166: 587). Plasmid DNA from B. subtilis and E. coli were prepared by the lysis method of Birnboim et al. (Nucl. Acid. Res., 1979, 7: 1513). Plasmid DNA transformation in B. subtilis was performed as described by Gryczan et al., (J. Bact., 1978, 134: 138).

Protease assays

Resorufin-labelled casein or $^{14}$C-casein was used for RP-III assays. Culture supernatant samples were assayed either 2 or 20 hours into stationary phase. Inhibitors were pre-incubated with the supernatant for 30 minutes at room temperature. Where a very small amount of residual protease activity was to be measured, $^{14}$C-casein or resorufin-labelled casein was used as the substrate.

In the $^{14}$C-casein test, culture supernatant (100 $\mu$l) was added to 100 $\mu$l of 50 mM Tris, 5 mM CaCl$_2$, pH 8, containing $1\times10^5$ cpm of $^{14}$C casein (New England Nuclear). The solutions were incubated at 37° C. for 30 minutes. The reactions were then placed on ice and 20 $\mu$g of BSA were added as carrier protein. Cold 10% TCA (600 $\mu$l) was added and the mix was kept on ice for 10 minutes. The solutions were centrifuged to spin out the precipitated protein and the supernatants counted in a scintillation counter.

The resorufin-labeled casein assay involved incubation of culture supernatant with an equal volume of resorufin-labelled casein in 50 mM Tris, 5 mM CaCl$_2$, pH 8.0, at 45° C. for 1 hour. Following incubation, unhydrolyzed substrate was precipitated with TCA and centrifuged. The supernatant (400 ml) was made alkaline with 500 mM Tris (pH 8.8) and the resulting chromogenic supernatant was quantitated spectrophotometrically at 574 nm.

Parental Strains

A number of Bacillus strains were used as sources for strains of the current invention.

Strain GP216, containing deletions within the four protease genes (apr, npr, isp-1, and epr), and strain GP240, containing deletions with the five protease genes (apr, npr, isp-1, epr, and bpr (rp-I)), were prepared as described by Sloma et al., EPA 0 369 817 A2. Strain GP241, isogenic to GP240 except for the hor gene, was constructed from strain GP216 by transformation of GP216 with a plasmid (pUC derivative called pJMhpr2, Perego and Hoch, J. Bacteriology 170:2560, 1988) containing a mutated hDr gene and a cat gene. hpr encodes a repressor of protease production in Bacillus. GP216 was transformed with pJMhpr2 and transformants were selected on chloramphenicol. Chromosomal DNA was extracted from chloramphenicol resistant colonies and analyzed by Southern hybridization. One clone was recovered which contained two copies of the hpr-2 gene resulting from a double crossover between homologous sequences on the vector and in the chromosome. The clone was grown in the absence of drug selection, and one chloramphenicol sensitive colony was designated BI114. Strain GP241 was constructed by introducing the deleted bpr (rp-I) gene into BI114 using the plasmid pKT3 in the same manner as described in Sloma et al. (EPA 0 369 817 A2) for the introduction of the deleted bpr (rp-I) gene into GP216 generating GP240.

Strain GP263, carrying a mutation in mpr was prepared from GP241 as follows. Plasmid pCR125, carrying the phleomycin resistance gene inserted in a deleted mpr gene (Sloma et al., EPA 0 369 817 A2), was digested with EcoR1 and the linear plasmid DNA was used to transform GP241 to phleomycin resistance. Resistant transformants were selected by plating the transformed cells onto TBAB plates containing a gradient of 0–5 µg/ml phleomycin across the plate. Transformants that were resistant to approximately 2.5 µg/ml phleomycin on the plates were single colony purified on TBAB phleomycin plates and thereafter grown on TBAB without selective antibiotic. One transformant isolated following this treatment was designated GP263.

GP263 was used to generate two additional strains, GP264 and GP275. GP264 has the sacQ* regulatory element chromosomally integrated via transformation with the plasmid pDP104, as described by Sloma et al., EPA 86308356.4. GP275 was produced by fully deleting the already-inactivated mpr (rp-II) gene from GP263. Since inactivation of mpr was due to an insertion of the phleomycin resistance gene into mpr, the deletion of mpr was accomplished by transformation of GP263 with a plasmid containing a deleted mpr and chloramphenicol resistance genes in contiguous array. Transformants were selected on chloramphenicol. Isolated colonies were then grown in the absence of selection and replica plated. GP275 was isolated as both choloramphenicol and phleomycin sensitive.

Identification of A Novel Proteolytic Activity

Extracellular protease levels are reduced in culture supernatants of Bacillus strains that do not express the proteases encoded by the six non-essential protease genes, apr, npr, isp-1 epr, bpr and mpr. When these deletions are present in a Spo+ host, there is an approximate 99% reduction in extracellular protease levels compared to the wild-type strain. In order to efficiently produce protease labile products in Bacillus, it is desirable to decrease or eliminate the remaining 1% residual protease activity.

Using the resorufin-labeled casein assay, a novel protease has been identified which is a major component of the residual activity in GP264. This protease may be classified as a serine protease by virtue of its quantitative inhibition by phenylmethylsulfonyl fluoride.

Isolation and Characterization of RP-III

A simple and efficient purification scheme was developed for the isolation of the RP-III protease from spent culture fluids. Cultures were grown in modified MRS lactobacillus media (Difco, with maltose substituted for glucose) and concentrated approximately 20-fold using an Amicon CH2PR system equipped with a S1Y10 spiral cartridge and dialyzed in place against 50 mM MES pH 5.5, and allowed to incubate overnight at 0°–4° C. The concentrated, crude supernatant containing precipitated protein was centrifuged (Sorvall GSA rotor, 9000 rpm, 30 minutes) and the resulting pellet containing 80–100% of the RP-III protease activity was resuspended in 100 mM Tris, pH 8. The reconstituted pellet was then applied to a 500 ml Superflo (Sepragen) column packed with Q-Sepharose (Pharmacia) equilibrated with 100 mM Tris, pH 8. Bound protein containing the RP-III protease was recovered from the column with a 50 mM MES, 2.5M KCl, pH 5.5, step elution.

The high-salt fractions containing protease activity were pooled, concentrated and dialyzed against 50 mM MOPS, pH 7, then applied to a 250 ml Superflo column of benzamidine Sepharose (Pharmacia) affinity resin equilibrated with the same buffer. Bound RP-III protease was eluted from the resin with a step of 50 mM MOPS, 1M KCl, pH 7. Proteolytically active high-salt fractions containing RP-III protease were pooled, concentrated and subjected to HPLC size-exclusion chromatography over a semi-preparative SW3000 column equilibrated with 50 mM MES, 200 mM KCl, pH 6.8. Protease activity was found exclusively in the void volume indicating the RP-III protease exists as part of a large aggregate. Finally, the size-excluded RP-III pool was concentrated, dialyzed against 20 mM sodium phosphate, 1M NaCl, 1 mM imidazole, pH 7.5, and fractionated over a Progel-TSK chelate-5PW HPLC column charged with Cu++. Activity was eluted with a linear gradient of imidazole to 20 mM.

Sodium dodecyl sulfate polyacrylamide gel electrophoresis (SDS-PAGE) revealed that the final pool of RP-III protease contained three major Coomassie-staining bands: one at 38.4 kDa and a doublet at 28.5 and 27.1 kDa. Each of these bands were electrophoretically transferred to and cut out of a sheet of PVDF membrane and subjected to amino-terminal sequence analysis. The sequence of the 28.5 kDa protein bore remarkable homology (81%) to a composite sequence of four other B. subtilis serine proteases (apr, subtilisin; epr, extracellular protease; bpr, Bacillopeptidase F, and isp-1, intracellular protease I) as well as to Bacillopeptidase F itself (65% homology). The proteolytic activity in this band is referred to herein as RP-III. FIG. 1 illustrates the amino-terminal sequence of RP-III and its comparison to a composite sequence deduced from the amino acid sequences of the aformentioned B. subtilis serine proteases.

All five proteases contain six identical residues spaced exactly the same within the N-termini, including the putative active center aspartic acid residue. Sequence analysis of the 27.1kDa lower band revealed it is most likely a proteolytic fragment of the 28.4kDa upper band since both proteins have identical amino-terminal sequences from residue 10 to residue 29. The loss of residues 1–9 on the lower 27.1kDa band accounts for its faster mobility on SDS-PAGE compared to the upper 28.4kDa band.

FIG. 2 shows the amino-terminal sequence obtained from RP-III and the sequence of the oligomeric probe constructed to identify the gene that codes for RP-III.

Cloning and Sequencing of the rp-III Gene

Genomic DNA was prepared from *Bacillus subtilis* GP275, and 10 µg were exhaustively digested with HindIII and probed with the guess-mer shown in FIG. 2. The probe hybridized to a 1 kb fragment of HindIII-digested genomic DNA; therefore, a 1 kb genomic library was prepared from size-selected fragments of 0.8–1.5 kb, using pUC19 as the vector. A clone carrying the rp-III gene was identified in the 1 kb library using standard hybridization techniques (Sambrook et al., 1989, Molecular Cloning, Cold Spring Harbor, N.Y.) and the guess-mer probe shown in FIG. 2. The plasmid isolated from this clone was designated pLLP1.

Southern blot analysis was used to determine the location of useful restriction sites with the rp-III gene (FIG. 3). Southern blots were performed using restriction digests of genomic DNA from GP275 and a probe encompassing the 1 kb HindIII fragment from pLLP1. These results led to the preparation of size-selected EcoR1, EcoR1/BglII, EcoR1/HindIII and BglII libraries from GP275 genomic DNA. Libraries yielding useful clones were prepared in either pIC20H or in pUC19 vectors digested with the apropriate restriction enzymes. pLLP4 and pLLP5 were isolated from 3kb and 0.5–0.8kb EcoR1/BglII pIC20H libraries, respectively, by screening with the 1 kb HindIII fragment of pLLP1. pLLP8 was isolated from a 0.5–0.8kb EcoRI/HindIII pUC19 library by screening with the 630 bp BglII fragment of pLLP5.

These clones were used to construct a restricion map of the rp-III gene, after the regions flanking the 1 kb HindIII fragment were identified. The DNA sequence was determined between the 5' BglII site of pLLP5 and approximately 1 kb beyond the 3' HindIII site of pLLP4 (FIGS. 3 and 4).

An open reading frame was found to extend 2457 nucleotides downstream from the 5' BglII site. A putative translation initiation codon was identified (FIG. 4, underlined nucleotides 40–42), with an accompanying ribosome binding site (FIG. 4, underlined nucleotides 25–32). The amino terminal sequence of the mature protein corresponding to the sequence in FIG. 2, was found at nucleotide 520 and is underlined in FIG. 4. From the sequence data of FIG. 4, the mature protein encoded by the rp-III gene is expected to contain 646 amino acids. Since the isolated protein has an apparent molecular weight of 28,000 d., this would suggest that RP-III undergoes extensive C-terminal processing or proteolysis.

Location of the rp-III Gene on the *B. Subtilis* Chromosome

Identification of the chromosomal location of the rp-III gene may be accomplished by standard methods, essentially as described by Sloma et al. EPA 0 369 817 A2, for other protease genes. Briefly, the location of the rp-III gene on the *B. subtilis* chromosome was mapped by integrating a drug resistance marker into the chromosome at the site of rp-III and using phage PBS1-mediated transduction to determine the location of the drug resistance gene. A fragment containing a neomycin resistance (neo) gene was cloned into the BglII site within the amino terminal coding region of rp-III, as described below to give plasmid pLLP2 which was used to create GP279. Southern blotting techniques and hybridization were used to confirm that the neo gene had integrated into the chromosome, interrupting the rp-III gene. Mapping experiments were then used to indicate that the inserted neo gene and rp-III are linked to the known Bacillus genetic locations, sacA, crtA, and epr, by PBS1 transduction.

Inactivation of the rp-III gene

It is often useful to inactivate the production of functional RP-III protease in microorganisms, particularly when a desired protein is being produced which is susceptible to RP-III proteolysis. The rp-III gene sequence provided herein allows for elimination of RP-III activity by any number of standard methods; including inactivation by insertion of nucleotide sequences into the gene, or by deletion of part or all of the native gene. In general, homologous recombinant techniques may be employed; for example, see Sloma et al. EPA 0 369 817 A2.

The rp-III gene was inactivated by creating an insertion mutation within the native gene. A 2.4kb SmaI to SmaI fragment containing the entire neomycin resistance gene was inserted into the Klenow blunt-ended BglII site of pLLP1, to give the plasmid pLLP2. pLLP2 was then linearized by ScaI digestion and used to transform Bacillus strain GP275. Neomycin resistant strains from this transformation were called GP279 and contained an inactivated rp-III gene. The inactivation of rp-III was confirmed by protease activity assay, as described above. Strains bearing the insertion mutation were otherwise normal with regard to sporulation and growth.

Heterologous DNA Expression

Cells in which the rp-III gene has been inactivated may be employed to express useful heterologous proteins. Such proteins would typically be of medical, agricultural, or industrial significance. In order to minimize any potential proteolytic damage of the heterologous protein, preferred cells will also be inactivated for apr, npr, epr, bpr. and mpr. Inactivation of additional genes such as isp1 and spoOA may also be useful.

DNA encoding the desired heterologous proteins must be engineered to contain the proper regulatory sequences including promoter, ribosome binding site, and transcription termination signals. In general, the DNA sequence encoding the protein and its accompanying regulatory sequences must be compatible with expression in the Bacillus host cell of the invention. The introduced DNA containing the expression sequences may reside within the cell in plasmid form or more preferably it may be chromosomally integrated.

The following references are incorporated herein by reference: Guidelines and references for heterologous protein expression and selection of appropriate Bacillus regulatory elements are given in Ganesan et al., 1986 *Bacillus Molecular Genetics and Biotechnology Applications. Academic press pp.* 367–493. Methods useful for the construction of expression vectors are given by Sambrook et al., 1989, *Molecular Cloning a Laboratory Manual* Cold Spring Harbor Laboratory Press.

Other Embodiments

Other embodiments are within the following claims. For example, in some instances it may be desirable to express, rather than mutate or delete, the gene encoding RP-III; for example, to produce the protease for purposes such as improvement of the cleaning activity of laundry detergents or for use in industrial processes. This can be accomplished either by inserting regulatory DNA (any appropriate Bacillus promoter and, if desired, ribosome binding site and/or signal encoding sequence) upstream of the protease-encoding gene or, alternatively, by inserting the protease-encoding gene into a Bacillus expression or secretion vector; the vector can then be transformed into a Bacillus strain for production (or secretion) of the protease, which is then isolated by conventional techniques. Alternatively, the protease can be overproduced by inserting one or more copies of the protease gene on a vector into a host strain containing a regulatory gene such as sacQ*.

---

We claim:

1. An isolated and purified Bacillus cell containing a mutation in the rp-III gene resulting in inhibition of the production by said cell of proteolytically active RP-III.

2. The Bacillus cell of claim 1, further comprising a mutation in each of one or more protease-encoding genes selected from the group: apr, npr, epr, bpr, and mpr, wherein each said mutation results in inhibition of the production by said cell of proteolytically active protease encoded by said gene.

3. The Bacillus cell of claim 2, each said mutation comprising a deletion within the coding region of said gene.

4. The Bacillus cell of claim 3, said cell further containing a mutation in the isp-1 gene encoding an intracellular protease.

5. The Bacillus cell of any of claims 1-4, said cell further containing a mutation which reduces said cell's capacity to produce one or more sporulation-dependent proteases.

6. The Bacillus cell of claim 5 wherein said sporulation-dependent protease mutation blocks sporulation at an early stage.

7. The Bacillus cell of claim 6, said sporulation-blocking mutation being in the spoOA gene.

8. The Bacillus cell of claim 7, said cell being *Bacillus subtilis*.

9. The Bacillus cell of any one of claims 1-4, further comprising a gene encoding a heterologous polypeptide.

10. The Bacillus cell of claim 5 further comprising a gene encoding a heterologous polypeptide.

11. A method for producing a heterologous polypeptide in a Bacillus cell, said method comprising introducing into said cell a gene encoding said heterologous polypeptide, modified to be expressed in said cell, said Bacillus cell containing mutations in the rp-III, apr and npr genes.

12. The method of claim 11 wherein said cell further contains mutations in one or more of the genes, epr, bpr, or mpr.

13. The method of claim 12, said cell further containing a mutation in the isp-1 gene encoding intracellular protease I.

14. The method of claim 11, 12, or 13 wherein said cell further contains a mutation which reduces said cell's capacity to produce one or more sporulation-dependent proteases, said mutation being in the spoOA gene.

15. The method of claim 14 wherein said cell is a *Bacillus subtilis* cell.

16. Purified DNA consisting essentially of a Bacillus rp-III gene.

17. A vector comprising a Bacillus rp-III gene and regulatory DNA operationally associated with said gene.

18. A Bacillus cell transformed with the vector of claim 17.

19. The DNA of claim 16 wherein said sequence is sequence ID No. 4 (FIG. 4).

* * * * *

UNITED STATES PATENT AND TRADEMARK OFFICE
CERTIFICATE OF CORRECTION

PATENT NO. : 5,294,542
DATED : March 15, 1994
INVENTOR(S) : Alan Sloma, et al

It is certified that error appears in the above-indentified patent and that said Letters Patent is hereby corrected as shown below:

Col. 4, line 60, replace "hor" with --hpr--;

Col. 4, line 64, replace "hDr" with --hpr--;

Col. 7, line 67, replace "crtA" with --ctrA--;

Signed and Sealed this

Sixth Day of September, 1994

Attest:

BRUCE LEHMAN

Attesting Officer      Commissioner of Patents and Trademarks

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
    ( A ) LENGTH: 25
    ( B ) TYPE: amino acid
    ( C ) STRANDEDNESS:
    ( D ) TOPOLOGY: linear ( x i ) SEQUENCE DESCRIPTION: SEQ ID NO: 1:

Ile Glu Ala Asn Asn Trp Asp Leu Gly Tyr Thr Gly Lys Gly Ile
                  5                   10                  15
Lys Val Ala Ile Ile Asp Thr Gly Val Glu
                  20                  25

( 2 ) INFORMATION FOR SEQ ID NO: 2:

( i ) SEQUENCE CHARACTERISTICS:
    ( A ) LENGTH: 35
    ( B ) TYPE: amino acid
    ( C ) STRANDEDNESS:
    ( D ) TOPOLOGY: linear ( x i ) SEQUENCE DESCRIPTION: SEQ ID NO: 2:

Met Asp Asp Ser Ala Pro Tyr Ile Gly Ala Asn Asp Ala Trp Asp
                  5                   10                  15
Leu Gly Tyr Thr Gly Lys Gly Ile Lys Val Ala Ile Ile Asp Thr
                  20                  25                  30
Gly Val Glu Tyr Asn
                  35

( 2 ) INFORMATION FOR SEQ ID NO: 3:

( i ) SEQUENCE CHARACTERISTICS:
    ( A ) LENGTH: 75
    ( B ) TYPE: nucleic acid
    ( C ) STRANDEDNESS: single
    ( D ) TOPOLOGY: linear ( x i ) SEQUENCE DESCRIPTION: SEQ ID NO: 3:

ATG GAT GAT TCT GCA CCG TAT ATT GGA GCA AAT GAT GCA TGG GAT    45
CTT GGA TAT ACA GGA AAA GGA ATT AAA GTT    75

( 2 ) INFORMATION FOR SEQ ID NO: 4:

( i ) SEQUENCE CHARACTERISTICS:
    ( A ) LENGTH: 2532 base pairs
    ( B ) TYPE: nucleic acid
    ( C ) STRANDEDNESS: single
    ( D ) TOPOLOGY: linear ( x i ) SEQUENCE DESCRIPTION: SEQ ID NO: 4:

ATCTTTCACA TTTTTTCTAA ATACAAAGGG GGAAACACA ATG AAA AAG GGG ATC    54
                                           Met Lys Lys Gly Ile
                                            1                 5

ATT CGC TTT CTG CTT GTA AGT TTC GTC TTA TTT TTT GCG TTA TCC ACA    102
Ile Arg Phe Leu Leu Val Ser Phe Val Leu Phe Phe Ala Leu Ser Thr
              10                  15                  20

| | | | | | | | | | | | | | | | | |
|---|---|---|---|---|---|---|---|---|---|---|---|---|---|---|---|---|
| GGC | ATT | ACG | GGC | GTT | CAG | GCA | GCT | CCG | GCT | TCT | TCA | AAA | ACG | TCG | GCT | 150 |
| Gly | Ile | Thr 25 | Gly | Val | Gln | Ala | Ala | Pro 30 | Ala | Ser | Ser | Lys | Thr 35 | Ser | Ala | |
| GAT | CTG | GAA | AAA | GCC | GAG | GTA | TTC | GGT | GAT | ATC | GAT | ATG | ACG | ACA | AGC | 198 |
| Asp | Leu | Glu 40 | Lys | Ala | Glu | Val | Phe 45 | Gly | Asp | Ile | Asp | Met 50 | Thr | Thr | Ser | |
| AAA | AAA | ACA | ACC | GTT | ATA | GTG | GAA | TTA | AAA | GAA | AAA | TCC | TTG | GCA | GAA | 246 |
| Lys | Lys | Thr 55 | Thr | Val | Ile | Val 60 | Glu | Leu | Lys | Glu | Lys 65 | Ser | Leu | Ala | Glu | |
| GCG | AAG | GAA | GCG | GGA | GAA | AGC | CAA | TCG | AAA | AGC | AAG | CTG | AAA | ACC | GCT | 294 |
| Ala | Lys 70 | Glu | Ala | Gly | Glu 75 | Ser | Gln | Ser | Lys | Ser 80 | Lys | Leu | Lys | Thr | Ala 85 | |
| CGC | ACC | AAA | GCA | AAA | AAC | AAA | GCA | ATC | AAA | GCA | GTG | AAA | AAC | GGA | AAA | 342 |
| Arg | Thr | Lys | Ala | Lys 90 | Asn | Lys | Ala | Ile | Lys 95 | Ala | Val | Lys | Asn | Gly 100 | Lys | |
| GTA | AAC | CGG | GAA | TAT | GAG | CAG | GTA | TTC | TCA | GGC | TTC | TCT | ATG | AAG | CTT | 390 |
| Val | Asn | Arg | Glu | Tyr 105 | Glu | Gln | Val | Phe | Ser 110 | Gly | Phe | Ser | Met | Lys 115 | Leu | |
| CCA | GCT | AAT | GAG | ATT | CCA | AAA | CTT | CTA | GCG | GTA | AAA | GAC | GTT | AAG | GCA | 438 |
| Pro | Ala | Asn | Glu 120 | Ile | Pro | Lys | Leu | Leu 125 | Ala | Val | Lys | Asp | Val 130 | Lys | Ala | |
| GTG | TAC | CCG | AAC | GTC | ACA | TAT | AAA | ACA | GAC | AAT | ATG | AAG | GAT | AAA | GAC | 486 |
| Val | Tyr 135 | Pro | Asn | Val | Thr | Tyr 140 | Lys | Thr | Asp | Asn | Met 145 | Lys | Asp | Lys | Asp | |
| GTC | ACA | ATC | TCC | GAA | GAC | GCC | GTA | TCT | CCG | CAA | ATG | GAT | GAC | AGT | GCG | 534 |
| Val 150 | Thr | Ile | Ser | Glu | Asp 155 | Ala | Val | Ser | Pro | Gln 160 | Met | Asp | Asp | Ser | Ala 165 | |
| CCT | TAT | ATC | GGA | GCA | AAC | GAT | GCA | TGG | GAT | TTA | GGC | TAC | ACA | GGA | AAA | 582 |
| Pro | Tyr | Ile | Gly | Ala 170 | Asn | Asp | Ala | Trp | Asp 175 | Leu | Gly | Tyr | Thr | Gly 180 | Lys | |
| GGC | ATC | AAG | GTG | GCG | ATT | ATT | GAC | ACT | GGG | GTT | GAA | TAC | AAT | CAC | CCA | 630 |
| Gly | Ile | Lys | Val 185 | Ala | Ile | Ile | Asp | Thr 190 | Gly | Val | Glu | Tyr | Asn 195 | His | Pro | |
| GAT | CTG | AAG | AAA | AAC | TTT | GGA | CAA | TAT | AAA | GGA | TAC | GAT | TTT | GTG | GAC | 678 |
| Asp | Leu | Lys 200 | Lys | Asn | Phe | Gly | Gln 205 | Tyr | Lys | Gly | Tyr | Asp 210 | Phe | Val | Asp | |
| AAT | GAT | TAC | GAT | CCA | AAA | GAA | ACA | CCA | ACC | GGC | GAT | CCG | AGG | GGC | GAG | 726 |
| Asn | Asp | Tyr 215 | Asp | Pro | Lys | Glu | Thr 220 | Pro | Thr | Gly | Asp | Pro 225 | Arg | Gly | Glu | |
| GCA | ACT | GAC | CAT | GGC | ACA | CAC | GTA | GCC | GGA | ACT | GTG | GCT | GCA | AAC | GGA | 774 |
| Ala | Thr 230 | Asp | His | Gly | Thr | His 235 | Val | Ala | Gly | Thr | Val 240 | Ala | Ala | Asn | Gly 245 | |
| ACG | ATT | AAA | GGC | GTA | GCG | CCT | GAT | GCC | ACA | CTT | CTT | GCT | TAT | CGT | GTG | 822 |
| Thr | Ile | Lys | Gly | Val 250 | Ala | Pro | Asp | Ala | Thr 255 | Leu | Leu | Ala | Tyr | Arg 260 | Val | |
| TTA | GGG | CCT | GGC | GGA | AGC | GGC | ACA | ACG | GAA | AAC | GTC | ATC | GCG | GGC | GTG | 870 |
| Leu | Gly | Pro | Gly 265 | Gly | Ser | Gly | Thr | Thr 270 | Glu | Asn | Val | Ile | Ala 275 | Gly | Val | |
| GAA | CGT | GCA | GTG | CAG | GAC | GGG | GCA | GAT | GTG | ATG | AAC | CTG | TCT | CTC | GGA | 918 |
| Glu | Arg | Ala 280 | Val | Gln | Asp | Gly | Ala 285 | Asp | Val | Met | Asn | Leu 290 | Ser | Leu | Gly | |
| AAC | TCT | TTA | AAC | AAC | CCG | GAC | TGG | GCG | ACA | AGC | ACA | GCG | CTT | GAC | TGG | 966 |
| Asn | Ser | Leu 295 | Asn | Asn | Pro | Asp | Trp 300 | Ala | Thr | Ser | Thr | Ala 305 | Leu | Asp | Trp | |
| GCC | ATG | TCA | GAA | GGC | GTT | GTC | GCT | GTT | ACC | TCA | AAC | GGC | AAC | AGC | GGA | 1014 |
| Ala | Met | Ser | Glu | Gly 315 | Val | Val | Ala | Val | Thr 320 | Ser | Asn | Gly | Asn | Ser 325 | Gly | |
| CCG | AAC | GGC | TGG | ACA | GTC | GGA | TCG | CCG | GGC | ACA | TCA | AGA | GAA | GCG | ATT | 1062 |
| Pro | Asn | Gly | Trp | Thr 330 | Val | Gly | Ser | Pro | Gly 335 | Thr | Ser | Arg | Glu | Ala 340 | Ile | |
| TCT | GTC | GGT | GCG | ACT | CAG | CTG | CCG | CTC | AAT | GAA | TAC | GCC | GTC | ACT | TTC | 1110 |
| Ser | Val | Gly | Ala | Thr | Gln | Leu | Pro | Leu | Asn | Glu | Tyr | Ala | Val | Thr | Phe | |

|  |  |  |  |  |  |  |  |  |  |  |  |  |  |  |  |  |
|---|---|---|---|---|---|---|---|---|---|---|---|---|---|---|---|---|
|  |  |  | 345 |  |  |  |  | 350 |  |  |  |  | 355 |  |  |  |
| GGC | TCC | TAC | TCT | TCA | GCA | AAA | GTG | ATG | GGC | TAC | AAC | AAA | GAG | GAC | GAC | 1158 |
| Gly | Ser | Tyr 360 | Ser | Ser | Ala | Lys | Val 365 | Met | Gly | Tyr | Asn | Lys 370 | Glu | Asp | Asp |  |
| GTC | AAA | GCG | CTC | AAT | AAC | AAA | GAA | GTT | GAG | CTT | GTC | GAA | GCG | GGA | ATC | 1206 |
| Val | Lys 375 | Ala | Leu | Asn | Asn | Lys 380 | Glu | Val | Glu | Leu | Val 385 | Glu | Ala | Gly | Ile |  |
| GGC | GAA | GCA | AAG | GAT | TTT | GAA | GGG | AAA | GAC | CTG | ACA | GGC | AAA | GTC | GCC | 1254 |
| Gly 390 | Glu | Ala | Lys | Asp | Phe 395 | Glu | Gly | Lys | Asp | Leu 400 | Thr | Gly | Lys | Val | Ala 405 |  |
| GTT | GTC | AAA | CGA | GGC | AGC | ATT | GCA | TTT | GTG | GAT | AAA | GCG | GAT | AAC | GCT | 1302 |
| Val | Val | Lys | Arg | Gly 410 | Ser | Ile | Ala | Phe | Val 415 | Asp | Lys | Ala | Asp | Asn 420 | Ala |  |
| AAA | AAA | GCC | GGT | GCA | ATC | GGC | ATG | GTT | GTG | TAT | AAC | AAC | CTC | TCT | GGA | 1350 |
| Lys | Lys | Ala | Gly 425 | Ala | Ile | Gly | Met | Val 430 | Val | Tyr | Asn | Asn | Leu 435 | Ser | Gly |  |
| GAA | ATT | GAA | GCC | AAT | GTG | CCA | GGC | ATG | TCT | GTC | CCA | ACG | ATT | AAG | CTT | 1398 |
| Glu | Ile | Glu 440 | Ala | Asn | Val | Pro | Gly 445 | Met | Ser | Val | Pro | Thr 450 | Ile | Lys | Leu |  |
| TCA | TTA | GAA | GAC | GGC | GAA | AAA | CTC | GTC | AGC | GCC | CTG | AAA | GCT | GGT | GAG | 1446 |
| Ser | Leu 455 | Glu | Asp | Gly | Glu | Lys 460 | Leu | Val | Ser | Ala | Leu 465 | Lys | Ala | Gly | Glu |  |
| ACA | AAA | ACA | ACA | TTC | AAG | TTG | ACG | GTC | TCA | AAA | GCG | CTC | GGT | GAA | CAA | 1494 |
| Thr 470 | Lys | Thr | Thr | Phe | Lys 475 | Leu | Thr | Val | Ser | Lys 480 | Ala | Leu | Gly | Glu | Gln 485 |  |
| GTC | GCT | GAT | TTC | TCA | TCA | CGC | GGC | CCT | GTT | ATG | GAT | ACG | TGG | ATG | ATT | 1542 |
| Val | Ala | Asp | Phe | Ser 490 | Ser | Arg | Gly | Pro | Val 495 | Met | Asp | Thr | Trp | Met 500 | Ile |  |
| AAG | CCT | GAT | ATT | TCC | GCG | CCA | GGG | GTC | AAT | ATC | GTG | AGC | ACG | ATC | CCA | 1590 |
| Lys | Pro | Asp | Ile | Ser 505 | Ala | Pro | Gly | Val | Asn 510 | Ile | Val | Ser | Thr 515 | Ile | Pro |  |
| ACA | CAC | GAT | CCT | GAC | CAT | CCA | TAC | GGC | TAC | GGA | TCA | AAA | CAA | GGA | ACA | 1638 |
| Thr | His | Asp 520 | Pro | Asp | His | Pro | Tyr 525 | Gly | Tyr | Gly | Ser | Lys 530 | Gln | Gly | Thr |  |
| AGC | ATG | GCA | TCG | CCT | CAT | ATT | GCC | GGA | GCG | GTT | GCC | GTT | ATT | AAA | CAA | 1686 |
| Ser | Met | Ala 535 | Ser | Pro | His | Ile 540 | Ala | Gly | Ala | Val | Ala 545 | Val | Ile | Lys | Gln |  |
| GCC | AAA | CCA | AAG | TGG | AGC | GTT | GAA | CAG | ATT | AAA | GCC | GCC | ATC | ATG | AAT | 1734 |
| Ala 550 | Lys | Pro | Lys | Trp | Ser 555 | Val | Glu | Gln | Ile | Lys 560 | Ala | Ala | Ile | Met | Asn 565 |  |
| ACC | GCT | GTC | ACT | TTA | AAG | GAT | AGC | GAT | GGG | GAA | GTA | TAT | CCG | CAT | AAC | 1782 |
| Thr | Ala | Val | Thr | Leu 570 | Lys | Asp | Ser | Asp | Gly 575 | Glu | Val | Tyr | Pro | His 580 | Asn |  |
| GCT | CAA | GGC | GCA | GGC | AGC | GCA | AGA | ATT | ATG | AAC | GCA | ATC | AAA | GCC | GAT | 1830 |
| Ala | Gln | Gly | Ala | Gly 585 | Ser | Ala | Arg | Ile | Met 590 | Asn | Ala | Ile | Lys 595 | Ala | Asp |  |
| TCG | CTC | GTC | TCA | CCT | GGA | AGC | TAT | TCA | TAC | GGC | ACG | TTC | TTG | AAG | GAA | 1878 |
| Ser | Leu | Val 600 | Ser | Pro | Gly | Ser | Tyr 605 | Ser | Tyr | Gly | Thr | Phe 610 | Leu | Lys | Glu |  |
| AAC | GGA | AAC | GAA | ACA | AAA | AAT | GAA | ACG | TTT | ACG | ATT | GAA | AAT | CAA | TCT | 1926 |
| Asn | Gly 615 | Asn | Glu | Thr | Lys | Asn 620 | Glu | Thr | Phe | Thr | Ile 625 | Glu | Asn | Gln | Ser |  |
| TCC | ATT | AGA | AAG | TCA | TAC | ACA | CTT | GAA | TAC | TCA | TTT | AAT | GGC | AGC | GGC | 1974 |
| Ser | Ile | Arg | Lys | Ser 635 | Tyr | Thr | Leu | Glu | Tyr 640 | Ser | Phe | Asn | Gly | Ser | Gly 645 |  |
| Ser 630 |  |  |  |  |  |  |  |  |  |  |  |  |  |  |  |  |
| ATT | TCC | ACA | TCC | GGC | ACA | AGC | CGT | GTT | GTG | ATT | CCG | GCA | CAT | CAA | ACC | 2022 |
| Ile | Ser | Thr | Ser | Gly 650 | Thr | Ser | Arg | Val | Val 655 | Ile | Pro | Ala | His | Gln 660 | Thr |  |
| GGG | AAA | GCC | ACT | GCA | AAA | GTA | AAG | GTC | AAT | ACG | AAG | AAA | ACA | AAA | GCT | 2070 |
| Gly | Lys | Ala | Thr 665 | Ala | Lys | Val | Lys | Val 670 | Asn | Thr | Lys | Lys | Thr 675 | Lys | Ala |  |

-continued

| | | | | | | | | | | | | | | | | |
|---|---|---|---|---|---|---|---|---|---|---|---|---|---|---|---|---|
| GGC | ACC | TAT | GAA | GGA | ACG | GTT | ATC | GTC | AGA | GAA | GGC | GGA | AAA | ACG | GTC | 2118 |
| Gly | Thr | Tyr | Glu | Gly | Thr | Val | Ile | Val | Arg | Glu | Gly | Gly | Lys | Thr | Val | |
| | | 680 | | | | | 685 | | | | | 690 | | | | |
| GCT | AAG | GTA | CCT | ACA | TTG | CTG | ATT | GTG | AAA | GAG | CCC | GAT | TAT | CCG | AGA | 2166 |
| Ala | Lys | Val | Pro | Thr | Leu | Leu | Ile | Val | Lys | Glu | Pro | Asp | Tyr | Pro | Arg | |
| | 695 | | | | | 700 | | | | | 705 | | | | | |
| GTC | ACA | TCT | GTC | TCT | GTC | AGC | GAA | GGG | TCT | GTA | CAA | GGT | ACC | TAT | CAA | 2214 |
| Val | Thr | Ser | Val | Ser | Val | Ser | Glu | Gly | Ser | Val | Gln | Gly | Thr | Tyr | Gln | |
| 710 | | | | | 715 | | | | | 720 | | | | | 725 | |
| ATT | GAA | ACC | TAC | CTT | CCT | GCG | GGA | GCG | GAA | GAG | CTG | GCG | TTC | CTC | GTC | 2262 |
| Ile | Glu | Thr | Tyr | Leu | Pro | Ala | Gly | Ala | Glu | Glu | Leu | Ala | Phe | Leu | Val | |
| | | | | 730 | | | | | 735 | | | | | 740 | | |
| TAT | GAC | AGC | AAC | CTT | GAT | TTC | GCA | GGC | CAA | GCC | GGC | ATT | TAT | AAA | AAC | 2310 |
| Tyr | Asp | Ser | Asn | Leu | Asp | Phe | Ala | Gly | Gln | Ala | Gly | Ile | Tyr | Lys | Asn | |
| | | | 745 | | | | | 750 | | | | | 755 | | | |
| CAA | GAT | AAA | GGT | TAC | CAG | TAC | TTT | GAC | TGG | GAC | GGC | ACG | ATT | AAT | GGC | 2358 |
| Gln | Asp | Lys | Gly | Tyr | Gln | Tyr | Phe | Asp | Trp | Asp | Gly | Thr | Ile | Asn | Gly | |
| | | 760 | | | | | 765 | | | | | 770 | | | | |
| GGA | ACC | AAA | CTT | CCG | GCC | GGA | GAG | TAT | TAC | TTG | CTC | GCA | TAT | GCC | GCG | 2406 |
| Gly | Thr | Lys | Leu | Pro | Ala | Gly | Glu | Tyr | Tyr | Leu | Leu | Ala | Tyr | Ala | Ala | |
| | 775 | | | | | 780 | | | | | 785 | | | | | |
| AAC | AAA | GGC | AAG | TCA | AGC | CAG | GTT | TTG | ACC | GAA | GAA | CCT | TTC | ACT | GTT | 2454 |
| Asn | Lys | Gly | Lys | Ser | Ser | Gln | Val | Leu | Thr | Glu | Glu | Pro | Phe | Thr | Val | |
| 790 | | | | | 795 | | | | | 800 | | | | | 805 | |
| GAA | TAAGAAAAAG | CCCTGCCGAT | TCGGCAGGGC | TTTTTAAAGA | TCAGTCAGCA | | | | | | | | | | | 2507 |
| Glu | | | | | | | | | | | | | | | | |

AACGCCTCCT GCAATAAGCG ATACG        2532